(12) United States Patent
Chudzik et al.

(10) Patent No.: US 10,575,833 B2
(45) Date of Patent: *Mar. 3, 2020

(54) BIOPSY APPARATUS HAVING INTEGRATED THUMBWHEEL MECHANISM FOR MANUAL ROTATION OF BIOPSY CANNULA

(71) Applicant: C. R. Bard, Inc., Tempe, AZ (US)

(72) Inventors: Rafal Chudzik, Peoria, AZ (US); Jason G. Seiger, Gilbert, AZ (US); Angela K. Jensen, Mesa, AZ (US); Glen V. Lazok, Mesa, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/593,739

(22) Filed: May 12, 2017

(65) Prior Publication Data
US 2017/0245840 A1    Aug. 31, 2017

Related U.S. Application Data

(60) Continuation of application No. 14/878,584, filed on Oct. 8, 2015, now Pat. No. 9,655,599, which is a division of application No. 13/388,370, filed as application No. PCT/US2009/053528 on Aug. 12, 2009, now Pat. No. 9,173,641.

(51) Int. Cl.
*A61B 10/02* (2006.01)

(52) U.S. Cl.
CPC ...... *A61B 10/0275* (2013.01); *A61B 10/0283* (2013.01); *A61B 2010/0208* (2013.01)

(58) Field of Classification Search
CPC ........................................... A61B 10/02–0283
See application file for complete search history.

(56) References Cited

U.S. PATENT DOCUMENTS

| 737,293 A | 8/1903 | Summerfeldt |
|---|---|---|
| 1,585,934 A | 5/1926 | Muir |
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |

(Continued)

FOREIGN PATENT DOCUMENTS

| CN | 101011268 A | 8/2007 |
|---|---|---|
| CN | 101032420 A | 9/2007 |

(Continued)

*Primary Examiner* — Devin B Henson
*Assistant Examiner* — H. Q. Nguyen

(57) ABSTRACT

A biopsy apparatus includes a housing, a biopsy cannula mounted to the housing, and a cannula rotation mechanism mounted to the housing. The cannula rotation mechanism has a thumbwheel, a first gear, and a second gear. The thumbwheel is configured to rotate about a rotational axis, with the rotational axis being perpendicular to the longitudinal axis of the biopsy cannula. The first gear is mounted in fixed attachment to the thumbwheel. The second gear is mounted in fixed attachment to the biopsy cannula. The first gear is in mesh with the second gear such that the first gear is directly drivably engaged with the second gear to rotate the biopsy cannula about the longitudinal axis when the thumbwheel is rotated.

12 Claims, 5 Drawing Sheets

(56) References Cited

U.S. PATENT DOCUMENTS

| | | |
|---|---|---|
| 3,289,669 A | 12/1966 | Dwyer et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,785,380 A | 1/1974 | Brumfield |
| 3,800,783 A | 4/1974 | Jamshidi |
| 3,844,272 A | 10/1974 | Banko |
| 3,882,849 A | 5/1975 | Jamshidi |
| 3,889,682 A | 6/1975 | Denis et al. |
| 3,916,948 A | 11/1975 | Benjamin |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,393,879 A | 7/1983 | Milgrom |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,706,687 A | 11/1987 | Rogers |
| 4,735,215 A | 4/1988 | Goto et al. |
| 4,776,346 A | 10/1988 | Beraha et al. |
| 4,792,327 A | 12/1988 | Swartz |
| 4,832,044 A | 5/1989 | Garg |
| 4,844,064 A | 7/1989 | Thimsen et al. |
| 4,844,087 A | 7/1989 | Garg |
| 4,850,354 A | 7/1989 | McGurk-Burleson et al. |
| 4,893,635 A | 1/1990 | de Groot et al. |
| 4,907,598 A | 3/1990 | Bauer |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,048,538 A | 9/1991 | Terwilliger et al. |
| 5,057,822 A | 10/1991 | Hoffman |
| 5,078,603 A | 1/1992 | Cohen |
| 5,125,413 A | 6/1992 | Baran |
| 5,138,245 A | 8/1992 | Mattinger et al. |
| 5,146,921 A | 9/1992 | Terwilliger et al. |
| 5,156,160 A | 10/1992 | Bennett |
| 5,158,528 A | 10/1992 | Walker et al. |
| 5,172,702 A | 12/1992 | Leigh et al. |
| 5,176,628 A | 1/1993 | Charles et al. |
| 5,183,052 A | 2/1993 | Terwilliger |
| 5,197,484 A | 3/1993 | Komberg et al. |
| 5,211,627 A | 5/1993 | William |
| 5,223,012 A | 6/1993 | Best et al. |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,254,117 A | 10/1993 | Rigby et al. |
| 5,282,476 A | 2/1994 | Terwilliger |
| 5,282,477 A | 2/1994 | Bauer |
| 5,290,253 A | 3/1994 | Kira |
| 5,305,762 A | 4/1994 | Acorn et al. |
| 5,324,306 A | 6/1994 | Makower et al. |
| 5,334,183 A | 8/1994 | Wuchinich |
| 5,335,671 A | 8/1994 | Clement |
| 5,368,029 A | 11/1994 | Holcombe et al. |
| 5,368,045 A | 11/1994 | Clement et al. |
| 5,383,874 A | 1/1995 | Jackson et al. |
| 5,397,462 A | 3/1995 | Higashijima et al. |
| 5,400,798 A | 3/1995 | Baran |
| 5,439,474 A | 8/1995 | Li |
| 5,458,112 A | 10/1995 | Weaver |
| 5,469,860 A | 11/1995 | De Santis |
| 5,471,994 A | 12/1995 | Guirguis |
| 5,479,486 A | 12/1995 | Saji |
| 5,485,917 A | 1/1996 | Early |
| 5,492,130 A | 2/1996 | Chiou |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,583 A | 2/1997 | Donahue et al. |
| 5,601,585 A | 2/1997 | Banik et al. |
| 5,602,449 A | 2/1997 | Krause et al. |
| 5,612,738 A | 3/1997 | Kim |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,779,649 A | 7/1998 | Herbert |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,871,699 A | 2/1999 | Ruggeri |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |

(56) References Cited

U.S. PATENT DOCUMENTS

| | | | |
|---|---|---|---|
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,032,673 A | 3/2000 | Savage et al. |
| 6,036,657 A | 3/2000 | Milliman et al. |
| 6,050,955 A | 4/2000 | Bryan et al. |
| 6,055,870 A | 5/2000 | Jaeger |
| 6,071,247 A | 6/2000 | Kennedy |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,152,918 A * | 11/2000 | Padilla ............... A61B 17/3403 606/15 |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,361,504 B1 | 3/2002 | Shin |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,461,302 B1 | 10/2002 | Thompson |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,494,844 B1 | 12/2002 | Van Bladel et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,586,585 B1 | 7/2003 | Bastian |
| 6,592,530 B1 | 7/2003 | Farhadi |
| 6,626,849 B2 | 9/2003 | Huitema et al. |
| 6,632,182 B1 | 10/2003 | Treat |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,702,832 B2 | 3/2004 | Ross et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,850,159 B1 | 2/2005 | Mudge |
| 6,860,860 B2 | 3/2005 | Viola |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,004,174 B2 | 2/2006 | Eggers et al. |
| 7,010,332 B1 | 3/2006 | Irvin et al. |
| 7,025,732 B2 | 4/2006 | Thompson et al. |
| D525,583 S | 7/2006 | Vu |
| 7,108,660 B2 | 9/2006 | Stephens et al. |
| 7,153,274 B2 | 12/2006 | Stephens et al. |
| 7,156,814 B1 | 1/2007 | Williamson, IV et al. |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,549,978 B2 | 6/2009 | Carlson et al. |
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,806,834 B2 | 10/2010 | Beckman et al. |
| 7,828,746 B2 | 11/2010 | Teague |
| 7,841,991 B2 | 11/2010 | Douglas et al. |
| 7,846,109 B2 | 12/2010 | Parihar et al. |
| 7,854,706 B2 | 12/2010 | Hibner |
| 7,862,517 B2 | 1/2011 | Tsonton et al. |
| 7,862,518 B2 | 1/2011 | Parihar |
| 7,871,384 B2 | 1/2011 | Thompson et al. |
| 7,883,476 B2 | 2/2011 | Miller et al. |
| 7,883,494 B2 | 2/2011 | Martin |
| 7,906,076 B2 | 3/2011 | Fischer |
| 7,914,462 B2 | 3/2011 | Hutchins et al. |
| 7,974,681 B2 | 7/2011 | Wallace et al. |
| 8,002,713 B2 | 8/2011 | Heske et al. |

(56) References Cited

U.S. PATENT DOCUMENTS

| | | |
|---|---|---|
| 8,012,102 B2 | 9/2011 | McCullough et al. |
| 8,016,772 B2 | 9/2011 | Heske et al. |
| 8,016,844 B2 | 9/2011 | Privitera et al. |
| 8,052,614 B2 | 11/2011 | Heske et al. |
| 8,052,615 B2 | 11/2011 | Reuber et al. |
| 8,057,402 B2 | 11/2011 | Hibner et al. |
| 8,073,008 B2 | 12/2011 | Mehta et al. |
| 8,075,495 B2 | 12/2011 | Andreyko et al. |
| 8,083,671 B2 | 12/2011 | Boulais et al. |
| 8,083,687 B2 | 12/2011 | Parihar |
| 8,109,885 B2 | 2/2012 | Heske et al. |
| 8,118,755 B2 | 2/2012 | Hibner et al. |
| 8,152,738 B2 | 4/2012 | Li et al. |
| 8,162,851 B2 | 4/2012 | Heske et al. |
| 8,172,771 B2 | 5/2012 | Miller et al. |
| 8,172,773 B2 | 5/2012 | Heske et al. |
| 8,187,204 B2 | 5/2012 | Miller et al. |
| 8,190,238 B2 | 5/2012 | Moll et al. |
| 8,206,409 B2 | 6/2012 | Privitera et al. |
| 8,251,916 B2 | 8/2012 | Speeg et al. |
| 8,277,393 B2 | 10/2012 | Miller et al. |
| 8,282,574 B2 * | 10/2012 | Coonahan .......... A61B 10/0275 600/564 |
| 8,287,465 B2 | 10/2012 | Hardin et al. |
| 8,313,444 B2 | 11/2012 | Thompson et al. |
| 8,343,069 B2 | 1/2013 | Uchiyama et al. |
| 8,430,825 B2 | 4/2013 | Mark |
| 8,430,827 B2 | 4/2013 | Nicoson et al. |
| 8,597,205 B2 | 12/2013 | Seiger et al. |
| 8,956,306 B2 | 2/2015 | Hibner |
| 9,421,002 B2 | 8/2016 | Heske et al. |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0000403 A1 | 1/2002 | Tanaka et al. |
| 2002/0029007 A1 | 3/2002 | Bryan et al. |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0115942 A1 | 8/2002 | Stanford et al. |
| 2002/0120212 A1 | 8/2002 | Ritchart et al. |
| 2002/0143269 A1 | 10/2002 | Neuenfeldt |
| 2002/0156395 A1 | 10/2002 | Stephens et al. |
| 2003/0023188 A1 | 1/2003 | Kritzman et al. |
| 2003/0023239 A1 | 1/2003 | Burbank et al. |
| 2003/0073929 A1 | 4/2003 | Baltschun et al. |
| 2003/0093103 A1 | 5/2003 | Malackowski et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0034280 A1 | 2/2004 | Privitera et al. |
| 2004/0049128 A1 | 3/2004 | Miller et al. |
| 2004/0054299 A1 | 3/2004 | Burdorff et al. |
| 2004/0082915 A1 | 4/2004 | Kadan |
| 2004/0092980 A1 | 5/2004 | Cesarini et al. |
| 2004/0092992 A1 | 5/2004 | Adams et al. |
| 2004/0162505 A1 | 8/2004 | Kaplan et al. |
| 2004/0167428 A1 | 8/2004 | Quick et al. |
| 2004/0186393 A1 | 9/2004 | Leigh et al. |
| 2004/0210161 A1 | 10/2004 | Burdorff et al. |
| 2004/0215103 A1 | 10/2004 | Mueller, Jr. et al. |
| 2004/0220495 A1 | 11/2004 | Cahir et al. |
| 2004/0230135 A1 | 11/2004 | Merkle |
| 2004/0230188 A1 | 11/2004 | Cioanta et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0054947 A1 | 3/2005 | Goldenberg |
| 2005/0065453 A1 | 3/2005 | Shabaz et al. |
| 2005/0085838 A1 | 4/2005 | Thompson et al. |
| 2005/0088120 A1 | 4/2005 | Avis |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 * | 7/2005 | Heske ............... A61B 10/0275 600/566 |
| 2005/0165329 A1 | 7/2005 | Taylor et al. |
| 2005/0177117 A1 | 8/2005 | Crocker et al. |
| 2005/0187489 A1 | 8/2005 | Wardle et al. |
| 2005/0193451 A1 | 9/2005 | Quistgaard et al. |
| 2005/0209530 A1 | 9/2005 | Pflueger |
| 2005/0215921 A1 | 9/2005 | Hibner et al. |
| 2005/0275378 A1 | 12/2005 | Canino et al. |
| 2005/0277829 A1 | 12/2005 | Tsonton et al. |
| 2005/0277871 A1 | 12/2005 | Selis |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0074350 A1 | 4/2006 | Cash |
| 2006/0113958 A1 | 6/2006 | Lobert et al. |
| 2006/0116603 A1 | 6/2006 | Shibazaki et al. |
| 2006/0122535 A1 | 6/2006 | Daum |
| 2006/0129063 A1 | 6/2006 | Thompson et al. |
| 2006/0149162 A1 | 7/2006 | Daw et al. |
| 2006/0178666 A1 | 8/2006 | Cosman et al. |
| 2006/0184063 A1 | 8/2006 | Miller |
| 2006/0200042 A1 | 9/2006 | Weikel, Jr. et al. |
| 2006/0241515 A1 | 10/2006 | Jones et al. |
| 2006/0258956 A1 | 11/2006 | Haberstich et al. |
| 2006/0260994 A1 | 11/2006 | Mark et al. |
| 2007/0016101 A1 | 1/2007 | Feldman et al. |
| 2007/0032741 A1 | 2/2007 | Hibner et al. |
| 2007/0032743 A1 | 2/2007 | Hibner |
| 2007/0055173 A1 | 3/2007 | DeLonzor et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 | 5/2007 | Stephens et al. |
| 2007/0118049 A1 | 5/2007 | Viola |
| 2007/0123797 A1 | 5/2007 | Krause |
| 2007/0158147 A1 | 7/2007 | Heske et al. |
| 2007/0161925 A1 | 7/2007 | Quick et al. |
| 2007/0167736 A1 | 7/2007 | Dietz et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0179401 A1 | 8/2007 | Hibner |
| 2007/0208271 A1 | 9/2007 | Voegele |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0292858 A1 | 12/2007 | Chen et al. |
| 2007/0293788 A1 | 12/2007 | Entrekin et al. |
| 2007/0293830 A1 | 12/2007 | Martin |
| 2008/0004545 A1 | 1/2008 | Garrison |
| 2008/0007217 A1 | 1/2008 | Riley |
| 2008/0021487 A1 | 1/2008 | Heisler |
| 2008/0021488 A1 | 1/2008 | Berberich |

(56) References Cited

U.S. PATENT DOCUMENTS

| | | |
|---|---|---|
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0079391 A1 | 4/2008 | Schroeck et al. |
| 2008/0103411 A1 | 5/2008 | Van Bladel et al. |
| 2008/0110261 A1 | 5/2008 | Randall et al. |
| 2008/0125634 A1 | 5/2008 | Ryan et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0015208 A1 | 1/2009 | White et al. |
| 2009/0030405 A1 | 1/2009 | Quick et al. |
| 2009/0048532 A1 | 2/2009 | Stephens et al. |
| 2009/0048533 A1 | 2/2009 | Miller |
| 2009/0062624 A1 | 3/2009 | Neville |
| 2009/0082695 A1 | 3/2009 | Whitehead |
| 2009/0087249 A1 | 4/2009 | Flagle et al. |
| 2009/0088666 A1 | 4/2009 | Miller et al. |
| 2009/0112118 A1 | 4/2009 | Quick, Jr. et al. |
| 2009/0125062 A1 | 5/2009 | Arnin |
| 2009/0137927 A1 | 5/2009 | Miller |
| 2009/0137929 A1 | 5/2009 | Mccullough et al. |
| 2009/0146609 A1 | 6/2009 | Santos |
| 2009/0171242 A1 | 7/2009 | Hibner |
| 2009/0171243 A1 | 7/2009 | Hibner et al. |
| 2009/0204022 A1 | 8/2009 | Schwindt |
| 2009/0227893 A1 | 9/2009 | Coonahan et al. |
| 2009/0247833 A1* | 10/2009 | Tanaka ............ G09B 23/285 600/188 |
| 2009/0281453 A1 | 11/2009 | Tsonton et al. |
| 2010/0030020 A1 | 2/2010 | Sanders et al. |
| 2010/0030108 A1 | 2/2010 | Anderson et al. |
| 2010/0063416 A1 | 3/2010 | Cicenas et al. |
| 2010/0102777 A1 | 4/2010 | Sa |
| 2010/0106053 A1 | 4/2010 | Videbaek et al. |
| 2010/0152610 A1 | 6/2010 | Parihar et al. |
| 2010/0152611 A1 | 6/2010 | Parihar et al. |
| 2010/0160820 A1 | 6/2010 | Weikel, Jr. et al. |
| 2010/0160823 A1 | 6/2010 | Parihar et al. |
| 2010/0160824 A1 | 6/2010 | Parihar et al. |
| 2010/0185179 A1 | 7/2010 | Chan |
| 2010/0210966 A1 | 8/2010 | Videbaek |
| 2010/0222700 A1 | 9/2010 | Hibner |
| 2010/0234760 A1 | 9/2010 | Almazan |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2010/0324449 A1 | 12/2010 | Rostaing et al. |
| 2011/0004119 A1 | 1/2011 | Hoffa et al. |
| 2011/0021946 A1 | 1/2011 | Heske et al. |
| 2011/0054350 A1 | 3/2011 | Videbaek |
| 2011/0077551 A1 | 3/2011 | Videbaek |
| 2011/0084109 A1 | 4/2011 | Ford et al. |
| 2011/0087131 A1 | 4/2011 | Videbaek |
| 2011/0105945 A1 | 5/2011 | Videbaek et al. |
| 2011/0105946 A1 | 5/2011 | Sorensen et al. |
| 2011/0152715 A1 | 6/2011 | Delap et al. |
| 2011/0160611 A1 | 6/2011 | Ritchart et al. |
| 2011/0208085 A1 | 8/2011 | Mccullough et al. |
| 2011/0224577 A1 | 9/2011 | Park |
| 2011/0295150 A1 | 12/2011 | Mccullough et al. |
| 2011/0313316 A1 | 12/2011 | Ranpura et al. |
| 2012/0065541 A1 | 3/2012 | Videbaek |
| 2012/0071787 A1 | 3/2012 | Reuber et al. |
| 2012/0095366 A1 | 4/2012 | Heske et al. |
| 2012/0130275 A1 | 5/2012 | Chudzik et al. |
| 2012/0184873 A1 | 7/2012 | Jorgensen et al. |
| 2012/0191009 A1 | 7/2012 | Hoon et al. |
| 2012/0203135 A1 | 8/2012 | Heske et al. |
| 2012/0215130 A1 | 8/2012 | Field et al. |
| 2012/0238905 A1 | 9/2012 | Heske et al. |
| 2012/0310109 A1 | 12/2012 | Almazan |
| 2012/0323120 A1 | 12/2012 | Taylor et al. |
| 2012/0323140 A1 | 12/2012 | Taylor et al. |
| 2012/0330185 A1 | 12/2012 | Coonahan et al. |
| 2013/0023789 A1 | 1/2013 | Anderson et al. |
| 2013/0023791 A1 | 1/2013 | Thompson et al. |
| 2013/0190648 A1 | 7/2013 | Videbaek |
| 2013/0197391 A1 | 8/2013 | Videbaek |
| 2013/0289441 A1 | 10/2013 | Videbaek et al. |
| 2014/0228706 A1 | 8/2014 | Mccullough et al. |
| 2014/0371585 A1 | 12/2014 | Thompson et al. |
| 2015/0018712 A1 | 1/2015 | Seiger et al. |
| 2015/0025415 A1 | 1/2015 | Videbaek et al. |
| 2015/0073301 A1 | 3/2015 | Videbaek et al. |
| 2015/0094613 A1 | 4/2015 | Jorgensen et al. |
| 2015/0133814 A1 | 5/2015 | Almazan |
| 2015/0148702 A1 | 5/2015 | Heske et al. |
| 2015/0190124 A1 | 7/2015 | Mccullough et al. |
| 2015/0223787 A1 | 8/2015 | Coonahan et al. |
| 2015/0238174 A1 | 8/2015 | Reuber et al. |
| 2016/0256138 A1 | 9/2016 | Videbaek et al. |
| 2016/0367229 A1 | 12/2016 | Jorgensen et al. |
| 2016/0367230 A1 | 12/2016 | Almazan |
| 2016/0374650 A1 | 12/2016 | Heske et al. |
| 2017/0042517 A1 | 2/2017 | Heske et al. |
| 2017/0181732 A1 | 6/2017 | Videbaek et al. |
| 2017/0258458 A1 | 9/2017 | Seiger et al. |
| 2018/0125467 A1 | 5/2018 | Reuber et al. |

FOREIGN PATENT DOCUMENTS

| | | |
|---|---|---|
| DE | 3924291 A1 | 1/1991 |
| DE | 4041614 C1 | 10/1992 |
| DE | 3924291 C2 | 7/2000 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0970658 A1 | 1/2000 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1604615 A1 | 12/2005 |
| EP | 1665989 A2 | 6/2006 |
| EP | 1698282 A1 | 9/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |
| GB | 2018601 A | 10/1979 |

(56) References Cited

FOREIGN PATENT DOCUMENTS

| | | | |
|---|---|---|---|
| JP | 2005530554 | A | 10/2005 |
| JP | 2006509545 | A | 3/2006 |
| JP | 2006528907 | A | 12/2006 |
| JP | 2007502159 | A | 2/2007 |
| WO | 9508945 | A2 | 4/1995 |
| WO | 9628097 | A1 | 9/1996 |
| WO | 9734531 | A1 | 9/1997 |
| WO | 9825522 | A1 | 6/1998 |
| WO | 9831285 | A1 | 7/1998 |
| WO | 9835615 | A1 | 8/1998 |
| WO | 9846290 | A1 | 10/1998 |
| WO | 9933501 | A1 | 7/1999 |
| WO | 0004832 | A1 | 2/2000 |
| WO | 0030546 | A1 | 6/2000 |
| WO | 0059378 | A2 | 10/2000 |
| WO | 0172230 | A1 | 10/2001 |
| WO | 0222023 | A1 | 3/2002 |
| WO | 0232318 | A1 | 4/2002 |
| WO | 02069808 | A2 | 9/2002 |
| WO | 2005013830 | A1 | 2/2005 |
| WO | 2006005342 | A1 | 1/2006 |
| WO | 2006015302 | A1 | 2/2006 |
| WO | 2007047128 | A1 | 4/2007 |
| WO | 2007095330 | A2 | 8/2007 |
| WO | 2007112751 | A2 | 10/2007 |
| WO | 2008021687 | A1 | 2/2008 |
| WO | 2008040812 | A1 | 4/2008 |
| WO | 2008131362 | A2 | 10/2008 |
| WO | 2010107424 | A1 | 9/2010 |
| WO | 2010120294 | A1 | 10/2010 |

* cited by examiner

BIOPSY APPARATUS HAVING INTEGRATED THUMBWHEEL MECHANISM FOR MANUAL ROTATION OF BIOPSY CANNULA

CROSS REFERENCE TO RELATED APPLICATIONS

This application is a continuation application of U.S. patent application Ser. No. 14/878,584, filed Oct. 8, 2015, now U.S. Pat. No. 9,655,599, which is a division of U.S. patent application Ser. No. 13/388,370, filed Feb. 1, 2012, now U.S. Pat. No. 9,173,641, which is a U.S. national phase of International Application No. PCT/US2009/053528, filed Aug. 12, 2009. Priority is claimed based on each of these applications, each of which is incorporated herein by reference in its entirety.

BACKGROUND OF THE INVENTION

1. Field of the Invention

The present invention relates to a biopsy apparatus, and, more particularly, to a biopsy apparatus having an integrated thumbwheel mechanism for manual rotation of a biopsy cannula.

2. Description of the Related Art

A biopsy may be performed on a patient to help in determining whether the cells in a biopsied region are cancerous. One biopsy technique used to evaluate breast tissue, for example, involves inserting a biopsy probe into the breast tissue region of interest to capture one or more tissue samples from the region. Such a biopsy technique often utilizes a vacuum to pull the tissue to be sampled into a sample notch of the biopsy probe, after which the tissue is severed and collected. One type of vacuum assisted biopsy apparatus includes a hand-held driver assembly having a vacuum source, and a disposable biopsy probe assembly configured for releasable attachment to the driver assembly. The biopsy probe typically includes a biopsy cannula, e.g., a needle, having a side port for receiving the tissue to be sampled.

During a biopsy procedure, it may be desirable to position the side port to various angular positions around a longitudinal axis of the biopsy cannula without having to rotate the hand-held driver assembly. One console-type biopsy device includes a control console tethered to a hand-held driver assembly, wherein the control module is programmed to provide automatic indexing of the side port to predetermined angular positions. However, such automatic indexing may limit the ability of the physician to make real-time changes and/or minute changes to the angular position of the side port.

Also, it is known to provide manual indexing of the side port of the biopsy cannula by attaching a knob to the distal end of the biopsy cannula, and then simply rotate the knob to position the side port to the desired angular position. One disadvantage, however, is that such an arrangement requires the physician to hold the handle of the hand-held driver assembly in one hand, while rotating the knob with the other hand.

SUMMARY OF THE INVENTION

The present invention provides a biopsy apparatus having a mechanism that enables a user to operate the biopsy apparatus and manually rotate a side port of a biopsy cannula to a desired rotational position about the longitudinal axis relative to the driver assembly through a single-handed operation of the biopsy apparatus. Mechanisms may also provide at least one of tactile, aural and visual feedback of the rotation of the biopsy cannula, as well as facilitate the selective locking of the biopsy cannula from further rotation so as to maintain a current rotational position of the side port of the biopsy cannula during the harvesting of a tissue sample.

As used herein, the terms "first" and "second" preceding an element name, e.g., first gear, second gear, etc., are for identification purposes to distinguish between different elements having similar characteristic, and are not intended to necessarily imply order, unless otherwise specified, nor are the terms "first" and "second" intended to preclude the inclusion of additional similar elements.

The invention in one form is directed to a biopsy apparatus. The biopsy apparatus includes a driver assembly having a housing configured to be grasped by a user. A biopsy probe mechanism is drivably coupled to the driver assembly. The biopsy probe mechanism includes a biopsy cannula having a cylindrical side wall, a proximal end, a distal end and a longitudinal axis extending between the proximal end and the distal end. The cylindrical side wall defines a lumen and has a side port located near the distal end that extends through the side wall to the lumen. A thumbwheel mechanism includes a thumbwheel mounted to the driver assembly to rotate about a first rotational axis, the first rotational axis being substantially perpendicular to the longitudinal axis, wherein at least a portion of the thumbwheel is exposed external to the housing. A first gear is mounted to the thumbwheel for coaxial rotation with the thumbwheel about the first rotational axis. A second gear is mounted to the biopsy cannula for coaxial rotation with the biopsy cannula about the longitudinal axis, the second gear being located to be drivably engaged by the first gear. A user grasps the housing and rotates the thumbwheel with a single hand to rotatably position the side port of the biopsy cannula at a desired rotational position about the longitudinal axis relative to the driver assembly.

The invention in another form is directed to a biopsy apparatus. The biopsy apparatus includes a driver assembly having a housing configured to be grasped by a user. A disposable biopsy probe mechanism is configured for releasable attachment to the driver assembly. The disposable biopsy probe mechanism is positioned at least partially within the housing when the disposable biopsy probe mechanism is attached to the driver assembly. The disposable biopsy probe mechanism includes a biopsy cannula having a cylindrical side wall, a proximal end, a distal end and a longitudinal axis extending between the proximal end and the distal end. The cylindrical side wall defines a lumen and has a side port located near the distal end that extends through the side wall to the lumen. The driver assembly includes a thumbwheel and a first gear, the thumbwheel and the first gear being coupled for unitary coaxial rotation about a first rotational axis. The first rotational axis is substantially perpendicular to the longitudinal axis. At least a portion of the thumbwheel is exposed external to the housing. The biopsy cannula includes a second gear configured for unitary coaxial rotation with the biopsy cannula about the longitudinal axis. The second gear is positioned to be drivably engaged by the first gear when the biopsy probe mechanism is attached to the driver assembly. A user rotates the thumbwheel while grasping the housing to effect a manual rotation of the biopsy cannula to position the side port of the biopsy cannula at a desired rotational position about the longitudinal axis relative to the driver assembly.

The invention in another form thereof is directed to a biopsy apparatus. The biopsy apparatus includes a driver assembly having a housing configured to be grasped by a user. A biopsy probe mechanism is drivably coupled to the driver assembly. The biopsy probe mechanism includes a biopsy cannula having a cylindrical side wall, a proximal end, a distal end and a longitudinal axis extending between the proximal end and the distal end. The cylindrical side wall defines a lumen and having a side port located near the distal end that extends through the side wall to the lumen. A thumbwheel mechanism is interposed between the driver assembly and the biopsy probe mechanism. The thumbwheel mechanism includes a thumbwheel drivably coupled to the biopsy cannula to rotatably position the side port of the biopsy cannula at a desired rotational position about the longitudinal axis relative to the driver assembly. A detent wheel is mounted to the biopsy cannula for coaxial rotation with the biopsy cannula about the longitudinal axis. The detent wheel has a circumferential surface and a plurality of detent recesses formed through the circumferential surface that extends radially toward the longitudinal axis. The plurality of detent recesses are positioned about the longitudinal axis at predetermined angular positions. An engagement device has an engagement element biased in constant engagement with the detent wheel, wherein as the biopsy cannula is rotated the engagement element rides along the circumferential surface of the detent wheel and produces at least one of a tactile and an aural feedback each time the engagement element engages one of the plurality of detent recesses.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate an embodiment of the invention, and such exemplifications are not to be construed as limiting the scope of the invention in any manner.

DETAILED DESCRIPTION OF THE INVENTION

Figure 1:
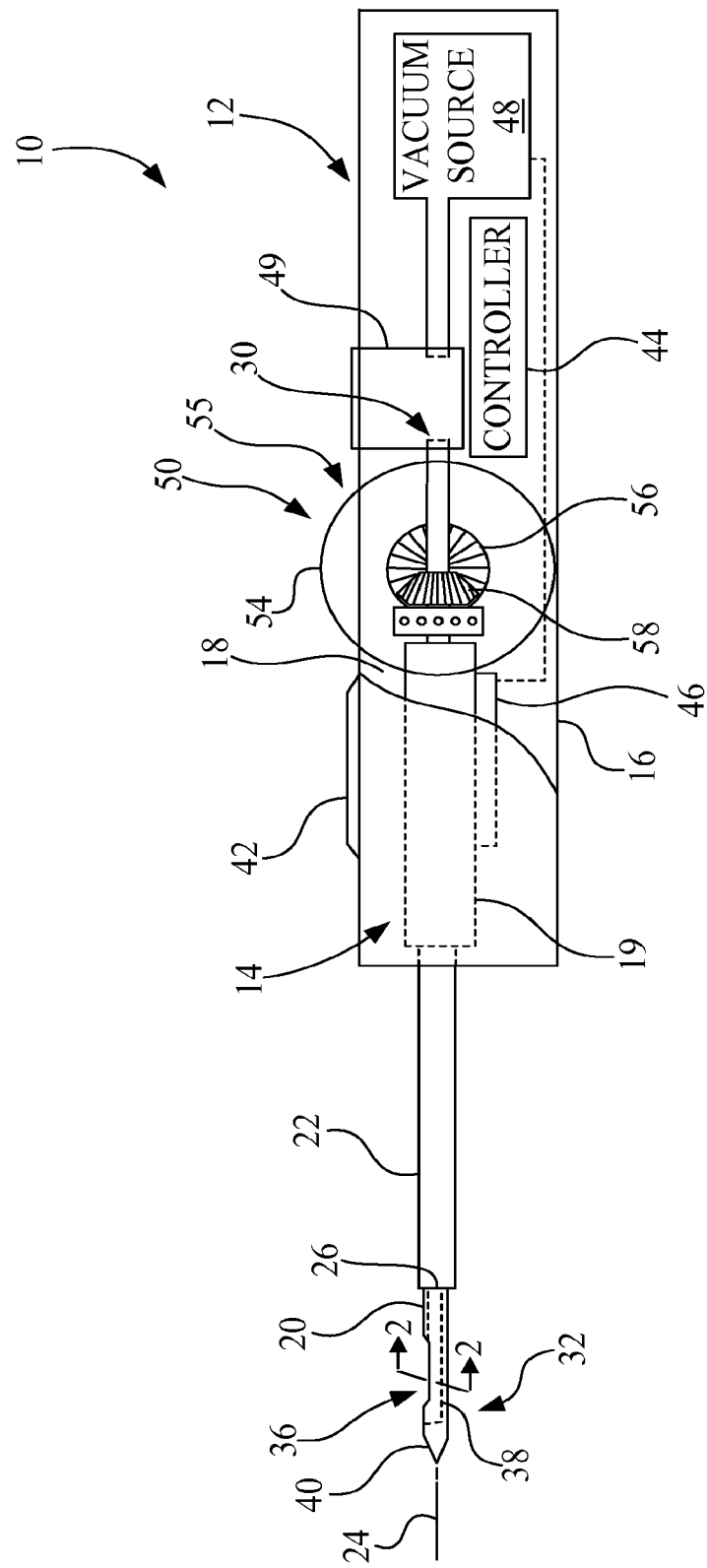
FIG. 1 is a side view of a biopsy apparatus configured in accordance with an embodiment of the present invention, with a biopsy probe mechanism mounted to a driver assembly, and with a side portion broken away to expose internal components which are schematically represented in part.

Referring now to the drawings, and more particularly to FIG. 1, there is shown a biopsy apparatus 10 which generally includes a driver assembly 12 and a biopsy probe mechanism 14.

Driver assembly 12 is configured to provide operative control over biopsy probe mechanism 14. Driver assembly 12 may be, for example, a non-disposable device, or alternatively a disposable device. As used herein, the term "non-disposable" is used to refer to a device that is intended for use on multiple patients during the lifetime of the device. Also, as used herein, the term "disposable" is used to refer to a device that is intended to be disposed of after use on a single patient.

Accordingly, in some embodiments driver assembly 12 and biopsy probe mechanism 14 may be releasably attached to one another. In other embodiments, however, it is contemplated that driver assembly 12 and biopsy probe mechanism 14 may be permanently attached to each other to form an integral biopsy apparatus, such that the entire biopsy apparatus is made to be disposable.

Driver assembly 12 includes a housing 16 configured, e.g., ergonomically designed, to be grasped by a user, e.g., a physician. Housing 16 defines a compartment 18 into which biopsy probe mechanism 14 is at least partially positioned when biopsy probe mechanism 14 is attached to driver assembly 12, with biopsy probe mechanism 14 being drivably coupled to driver assembly 12.

Biopsy probe mechanism 14 is generally intended to be disposable as a unit. In the present embodiment, biopsy probe mechanism 14 is configured for releasable attachment to driver assembly 12. As used herein, the term "releasable attachment" means a configuration that facilitates an intended temporary connection followed by selective detachment involving a manipulation of disposable biopsy probe mechanism 14 relative to driver assembly 12, e.g., without the need for tools. Biopsy probe mechanism 14 includes a frame 19 to which a biopsy cannula 20 and a cutting cannula 22 are mounted. Biopsy cannula 20 and a cutting cannula 22 are arranged coaxially with respect to a longitudinal axis 24.

Cutting cannula 22 has a distal cutting end 26.

Figure 2:
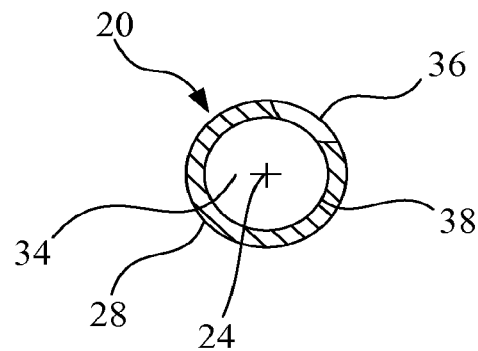
FIG. 2 is a section view of a biopsy cannula of the biopsy apparatus of FIG. 1, taken along line 2-2 of FIG. 1.

Referring to FIGS. 1 and 2, biopsy cannula 20 has a cylindrical side wall 28 having a proximal end 30 and a distal end 32, wherein the longitudinal axis 24 extends between the proximal end 30 and the distal end 32. Cylindrical side wall 28 defines a lumen 34 and has a side port 36 located near distal end 32. Side port 36 extends through the side wall to the lumen 34 to a portion of the lumen 34 referred to as the sample chamber, or basket, 38. Biopsy cannula 20 may, for example, be in the form of a hollow needle having a piercing tip 40.

Driver assembly 12 further includes a user interface 42 located to be externally accessible to the user with respect to housing 16 for receiving operation commands from the user, e.g., through one or more pushbuttons, and may also include a display, e.g., one or more lights or an LCD (liquid crystal display), to display information to the user. A controller 44 is communicatively coupled user interface 42. Controller 44 may include, for example, a microprocessor and associated memory (not shown) for executing program instructions to perform functions associated with the harvesting of biopsy tissue samples during a biopsy procedure.

There is contained within housing 16 an electromechanical drive 46 and a vacuum source 48. Electromechanical drive 46 is connected in electrical communication with controller 44. Electromechanical drive 46 is further drivably coupled (illustrated by dashed lines) to the biopsy probe mechanism 14 and to the vacuum source 48 to selectively and operatively control vacuum source 48 and/or cutting cannula 22. Electromechanical drive 46 may include, for example, one or more of a linear drive that converts rotational motion to linear motion (e.g., a worm gear arrangement, rack and pinion arrangement, solenoid-slide arrangement, etc.) and a rotational drive that may include one or more of a gear, gear train, belt/pulley arrangement, etc., for effecting operation of cutting cannula 22 of biopsy probe mechanism 14 and/or vacuum source 48.

Vacuum source 48 may be, for example, a peristaltic pump, a diaphragm pump, syringe-type pump, etc. Vacuum source 48 may be permanently integrated into driver assembly 12, or alternatively may be permanently integrated as a part of the biopsy probe mechanism 14. In either case, vacuum source 48 is coupled in fluid communication with lumen 34 of biopsy cannula 20.

During a biopsy procedure, for example, biopsy cannula 20 and cutting cannula 22 are relatively positioned such that side port 36 is closed by cutting cannula 22. Biopsy cannula 20 and cutting cannula 22 are advanced into the tissue region to be sampled of a patient. Commands are sent via user interface 42 to electromechanical drive 46 to open side port 36 by retracting cutting cannula 22 along longitudinal axis 24, and to operate vacuum source 48 so as to selectively draw tissue though side port 36 of biopsy cannula 20 into sample chamber 38. Once tissue is received through side port 36, electromechanical drive 46 is controlled to cause cutting cannula 22 to advance linearly along longitudinal axis 24 to close side port 36 and sever the tissue prolapsed into sample chamber 38. In some circumstances, it may be desirable for electromechanical drive 46 to cause cutting cannula 22 to rotate or oscillate during the linear advancement. The severed tissue may then be advanced to a tissue collection receptacle 49, such as for example by vacuum, where the tissue samples may be retrieved. Alternatively, in an embodiment wherein vacuum source 48 is in direct fluid communication with lumen 34 (i.e., to the exclusion of tissue collection receptacle 49), each of the tissue samples may simply be retained in lumen 34 of biopsy cannula 20.

Figure 5:
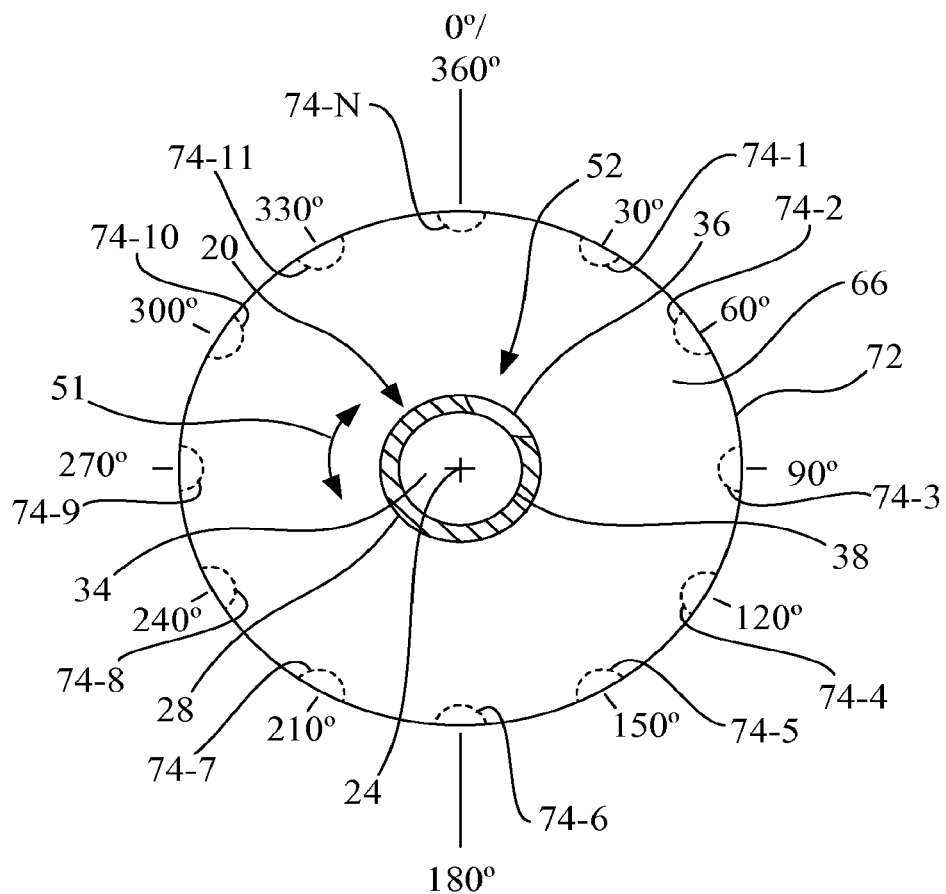
FIG. 5 is a section view of the biopsy cannula coupled to the detent wheel of the positioning mechanism of FIG. 3, taken along line 5-5 of FIG. 3.
Figure 3:
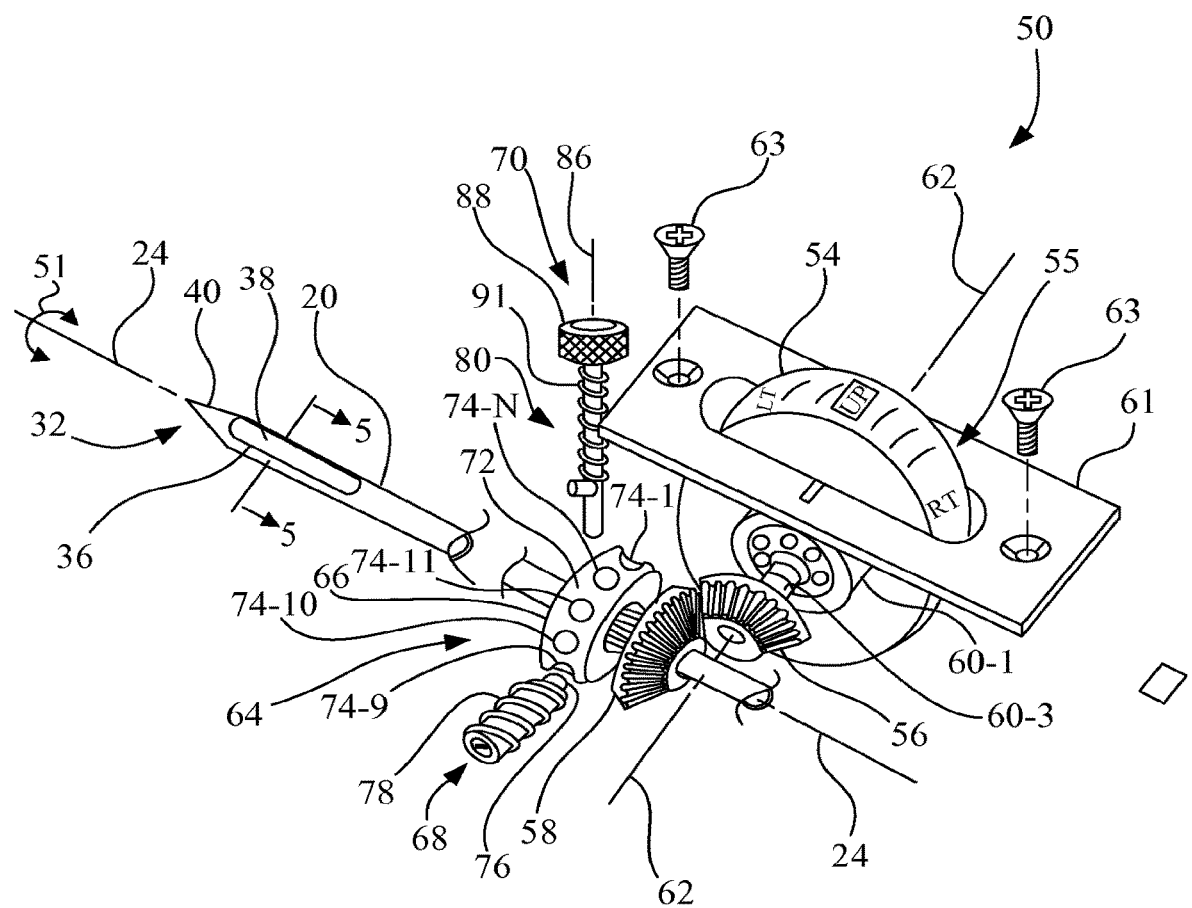
FIG. 3 is a perspective view of the thumbwheel mechanism of the biopsy apparatus of FIG. 1, which includes positioning and locking mechanisms.
Figure 4:
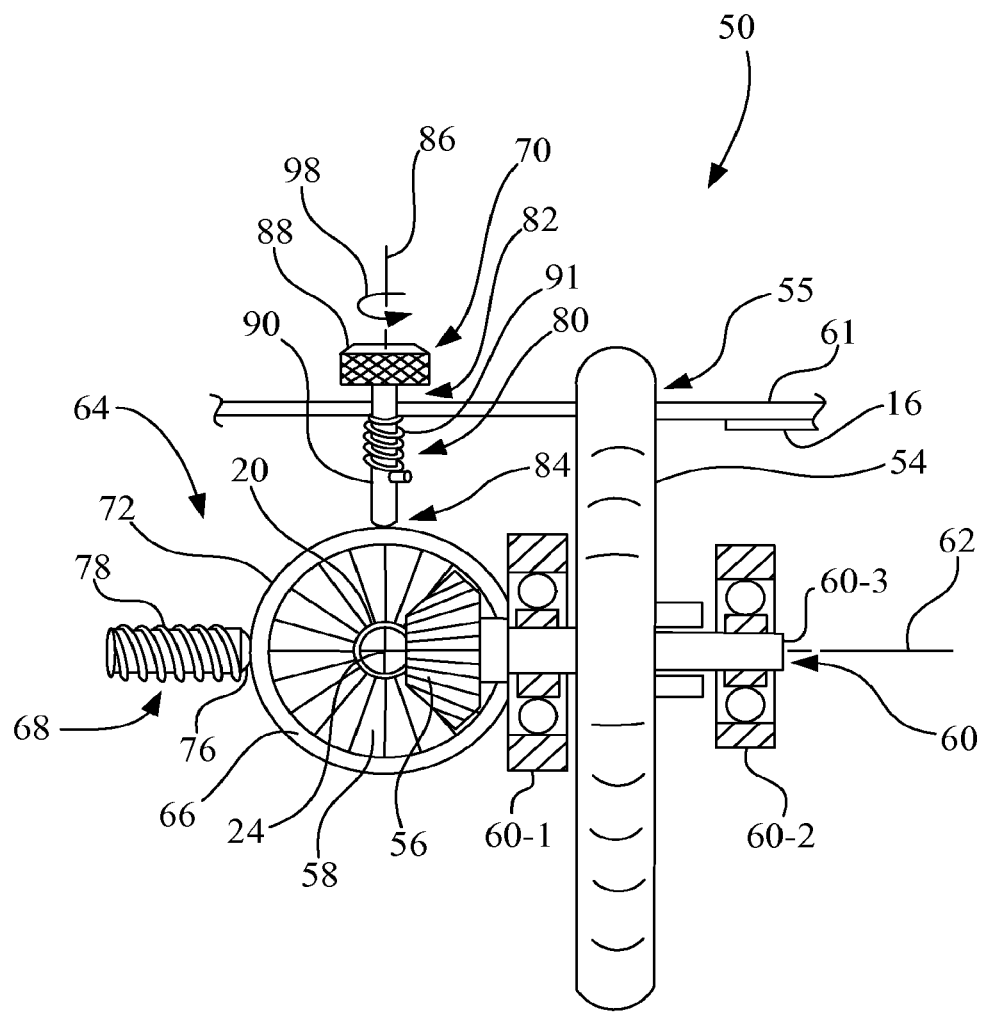
FIG. 4 is rear view of the thumbwheel mechanism of FIG. 3.

Referring also to FIGS. 3-5, further convenience may be provided to the user by the inclusion of a thumbwheel mechanism 50 interposed between driver assembly 12 and biopsy probe mechanism 14 to facilitate a manual rotation of biopsy cannula 20 relative to driver assembly 12. The rotation of biopsy cannula 20 may be in either the clockwise or counterclockwise directions, as indicated by double-headed arrow 51. More particularly, a user may grasp housing 16 of driver assembly 12 with a single hand and may operate thumbwheel mechanism 50 with a thumb or finger of the same hand to rotatably position side port 36 of biopsy cannula 20 at a desired rotational position, e.g. rotational position 52, about longitudinal axis 24 relative to driver assembly 12, wherein the desired rotational position 52 is an angular value, e.g., 30 degrees in the present example, in a range of angular values from 0 degrees to 360 degrees, inclusive, as illustrated in FIG. 5.

As best shown in FIGS. 3 and 4, thumbwheel mechanism 50 includes a thumbwheel 54, a first gear 56 and a second gear 58. Each of first gear 56 and second gear 58 may be, for example, a bevel gear.

Thumbwheel 54 and first gear 56 is rotatably mounted to driver assembly 12 by an axle/bearings arrangement 60, including bearings 60-1, 60-2 and axle 60-3, to rotate about a first rotational axis 62. The unit formed by thumbwheel 54, first gear 56 and axle/bearing arrangement 60 may be mounted to housing 16 of driver assembly 12 via a mounting plate 61 and a pair of screws 63. First rotational axis 62 is positioned to be substantially perpendicular to longitudinal axis 24. As shown in FIGS. 1 and 4, at least a portion 55 of thumbwheel 54 is exposed external to housing 16 of driver assembly 12.

First gear 56 is coupled, e.g., mounted in fixed attachment, to thumbwheel 54 for unitary coaxial rotation with thumbwheel 54 about first rotational axis 62. Second gear 58 is coupled, e.g., mounted in fixed attachment, to biopsy cannula 20 for unitary coaxial rotation with biopsy cannula 20 about longitudinal axis 24. As shown, second gear 58, and in turn biopsy probe mechanism 14, is located to be drivably engaged by first gear 56 when said biopsy probe mechanism 14 is attached to driver assembly 12.

Accordingly, the user grasps housing 16 and rotates thumbwheel 54 with a single hand to effect a manual rotation of biopsy cannula 20 to thereby rotatably position side port 36 of biopsy cannula 20 at a desired rotational position, e.g., rotational position 52, about longitudinal axis 24 relative to driver assembly 12 in a range of 0 degrees through 360 degree, as illustrated in FIG. 5. Thumbwheel 54 may include an indicia, e.g., "UP", located on the periphery of thumbwheel 54 to coincide with the designated "up" position, i.e., the 0/360 degree position of side port 36 (see FIG. 5). As also shown in FIG. 3, other indicia, such as "LT" for left and "RT" for right, may be included to aid in indicating the rotational direction of biopsy cannula 20.

Thumbwheel mechanism 50 may further include a positioning mechanism 64 coupled to said biopsy cannula 20 to provide resistive positioning of side port 36 of biopsy cannula 20 at discrete angular positions about longitudinal axis 24, and may further provide at least one of tactile and aural feedback to the user as biopsy cannula 20 is rotated about longitudinal axis 24 relative to driver assembly 12.

Referring to FIGS. 3-5, positioning mechanism 64 includes a detent wheel 66, an engagement device 68, and a lock mechanism 70. While the present embodiment includes both engagement device 68 and lock mechanism 70, it is contemplated that alternatively it may be desirable to have only one of engagement device 68 and lock mechanism 70 without the other. In such an alternative, one of engagement device 68 and lock mechanism 70 would simply be deleted from the design.

Detent wheel 66 is mounted to biopsy cannula 20 for unitary coaxial rotation with biopsy cannula 20 about longitudinal axis 24. Detent wheel 66 has a circumferential surface 72 and a plurality of detent recesses 74-1, 74-1 . . . 74-N formed through circumferential surface 72 and extending radially toward longitudinal axis 24, wherein "N" is the total number of detents and is a positive integer. Each of the plurality of detent recesses 74-1 through 74-N may be formed, for example, as a cup-shaped void having a tapered side wall that is curved or a frustoconical.

The plurality of detent recesses 74-1 through 74-N are positioned about longitudinal axis 24 at predetermined angular positions, as illustrated in FIG. 5. In the present exemplary embodiment, the plurality of detent recesses 74-1 through 74-N are arranged in uniform angular increments of 30 degrees, and thus the number of detents is N=12. However, for more coarse angular increments N may be less than 12 and for finer (more minute) angular increments N may be greater than 12, as desired.

Engagement device 68 is mounted to biopsy probe mechanism 14, such as to frame 19. Engagement device 68 includes an engagement element 76 biased by a spring 78 to be in constant engagement with detent wheel 66. Engagement element 76 may be, for example a metallic ball or plug having a rounded or tapered end. Spring 78 may be, for example a coil spring, leaf spring, etc. Thus, as biopsy cannula 20 is rotated, engagement element 76 rides along circumferential surface 72 of detent wheel 66 and produces a resistive positioning of biopsy cannula 20, which is experienced by the user as a tactile interruption and/or aural feedback (e.g., a click sound) each time engagement element 76 engages one of the plurality of detent recesses 74-1 through 74-N of detent wheel 66.

Also, in some biopsy applications as illustrated in FIG. 5, the plurality of detent recesses 74-1 through 74-N may be positioned about longitudinal axis 24 at uniform angular increments and be of a sufficient population N such that an opening defined by side port 36 at a current position (e.g., 74-1) will overlap with the opening of side port 36 at a next position (e.g., 74-2) at each of the angular increments, whereby providing a full 360 degrees of sampling capability.

In general, lock mechanism 70 includes a locking pin 80 having a proximal end 82 and an engagement end 84, and is longitudinally arranged along a locking axis 86. A head portion 88 is attached, or formed integral with, the proximal end 82 of locking pin 80. A shaft portion 90 extends from head portion 88 toward engagement end 84. A spring 91 biases locking pin 80 along locking axis 86 toward detent wheel 66.

Thus, locking pin 80 is configured for linear movement along locking axis 86 relative to circumferential surface 72 of detent wheel 66 for selective locking engagement of engagement end 84 with one of the plurality of detent recesses 74-1 through 74-N of detent wheel 66 to prevent a rotation of biopsy cannula 20 from a current angular position of side port 36 of biopsy cannula 20 relative to driver assembly 12.

Figure 6A:
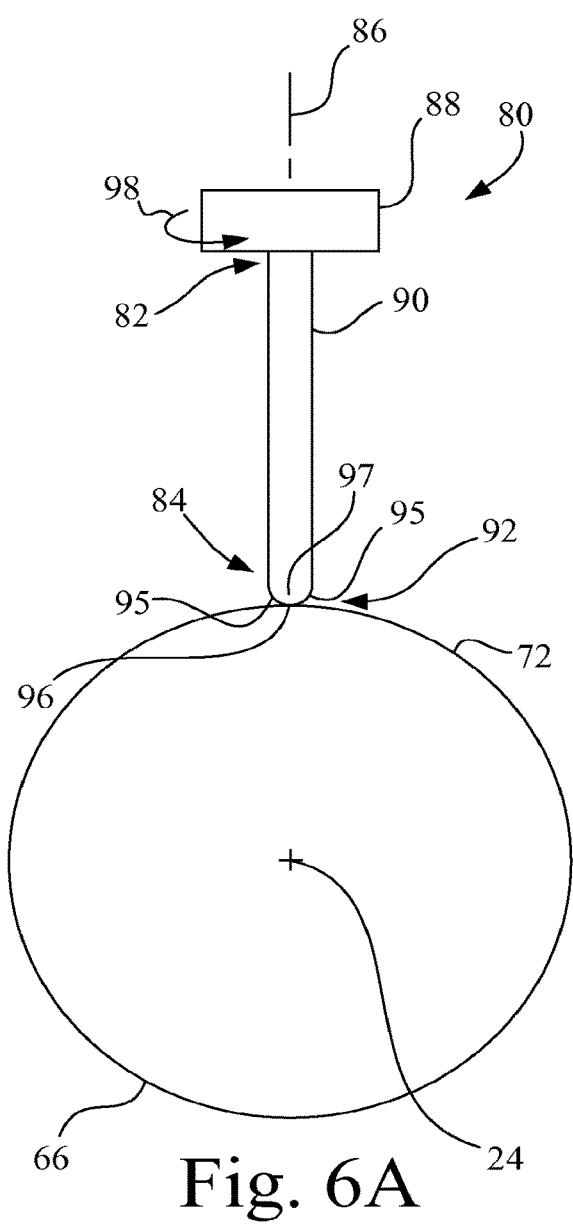
FIG. 6A is a side view of a portion of the locking mechanism of FIGS. 3 and 4 with the locking pin in the unlocked rotational position.
Figure 6B:
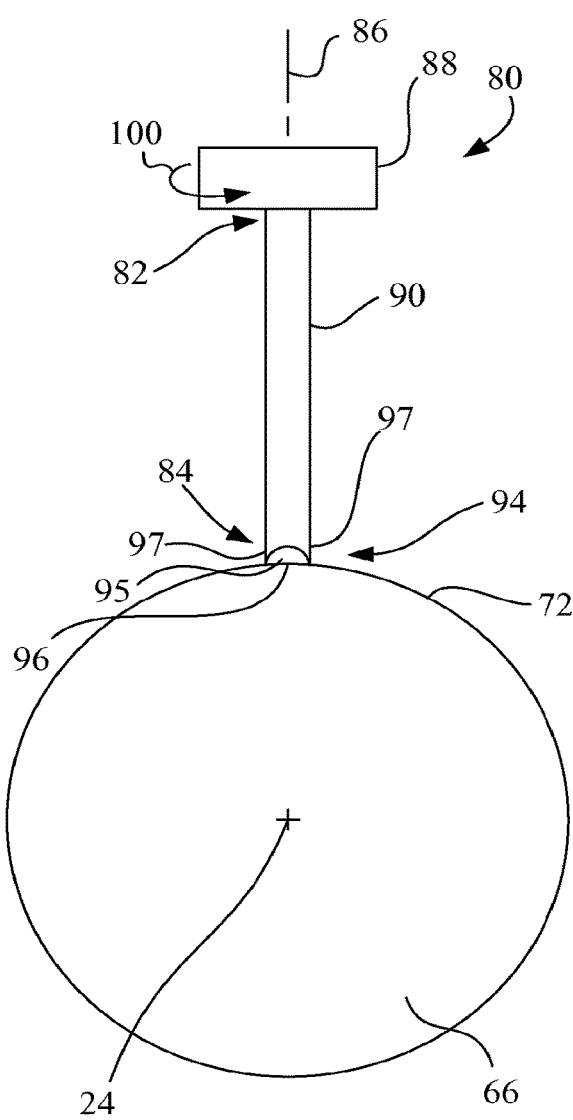
FIG. 6B is a side view of a portion of the locking mechanism of FIGS. 3 and 4 with the locking pin in the locking rotational position.

Referring also to FIGS. 6A and 6B, engagement end 84 of locking pin 80 may have a tapered portion 92 and a non-tapered portion 94 angularly offset, e.g., at 90 degrees, from tapered portion 92 about locking axis 86. In the present embodiment, tapered portion 92 may have a curved or beveled faces 95 that smoothly transitions to the tip end 96 of engagement end 84, and the non-tapered portion 94 may have a straight faces 97 that abruptly transition, e.g., at 90 degrees, to the tip end 96 of engagement end 84.

In operation, for example, when locking pin 80 is positioned in an unlocked rotational position 98 relative to locking axis 86 and detent wheel 66, as illustrated in FIG. 6A, engagement end 84 rides along circumferential surface 72 of detent wheel 66 and tapered portion 92 sequentially passes into and out of a respective detent recess of the plurality of detent recesses 74-1 through 74-N of detent wheel 66 (see also FIGS. 3-5) as biopsy cannula 20 is rotated, thereby operating similarly to engagement device 68 in providing a positioning mechanism that provides at least one of aural, visual and tactile feedback of a progressive rotation of biopsy cannula 20.

However, when locking pin 80 is positioned in a locking rotational position 100 relative to locking axis 86 and detent wheel 66, as illustrated in FIG. 6B, as biopsy cannula 20 is rotated engagement end 84 rides along circumferential surface 72 of detent wheel 66 and non-tapered portion 94 lockably engages a next encountered detent recess of the plurality of detent recesses 74-1 through 74-N of detent wheel 66 (see also FIGS. 3-5) to lock biopsy cannula 20 from further rotation. Locking pin 80 is released from locking rotational position 100 by a further 90 degree rotation of locking pin 80 relative to locking axis 86, in either rotational direction, to unlocked rotational position 98.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy apparatus, comprising:
   a housing;
   a biopsy cannula mounted to the housing, the biopsy cannula having a side wall, a proximal end, a distal end, and a longitudinal axis extending between the proximal end and the distal end, the side wall having an exterior surface and an interior surface, the interior surface of the side wall defining a lumen, and the side wall having a side port proximal to the distal end that extends through the side wall to the lumen;
   a cannula rotation mechanism mounted to the housing, the cannula rotation mechanism having a thumbwheel, a first gear, and a second gear,
     the thumbwheel configured to rotate about a rotational axis, the rotational axis being perpendicular to the longitudinal axis of the biopsy cannula,
     the first gear mounted in fixed attachment to the thumbwheel,
     the second gear mounted in fixed attachment to the exterior surface of the side wall of the biopsy cannula, and
     the first gear being in mesh with the second gear such that the first gear is directly drivably engaged with the second gear to rotate the biopsy cannula about the longitudinal axis when the thumbwheel is rotated;
   a detent wheel mounted in fixed attachment to the biopsy cannula, the detent wheel having a plurality of detent recesses positioned about the longitudinal axis at predetermined angular positions; and
   an engagement element biased by a spring to be in constant engagement with the detent wheel to sequentially engage each of the plurality of detent recesses to produce at least one of tactile and aural feedback each time the engagement element engages one of the plurality of detent recesses.

2. The biopsy apparatus of claim 1, wherein the biopsy cannula and the cannula rotation mechanism are configured as a disposable biopsy probe, the disposable biopsy probe configured for releasable attachment to the housing.

3. The biopsy apparatus of claim 1, configured such that a user rotates the thumbwheel while grasping the housing to effect a manual rotation of the biopsy cannula to position the side port of the biopsy cannula at a desired rotational position about the longitudinal axis.

4. The apparatus of claim 1, further comprising a cutting cannula mounted to the housing, wherein:
   the cutting cannula and the biopsy cannula are arranged coaxially with respect to the longitudinal axis of the biopsy cannula,
   the biopsy cannula is disposed inside the cutting cannula, and the thumbwheel is configured to rotate the biopsy cannula about the longitudinal axis relative to the cutting cannula.

5. The apparatus of claim 4, wherein the cutting cannula is configured for linear advancement and linear retraction along the longitudinal axis.

6. A biopsy apparatus, comprising:
a housing;
a biopsy cannula mounted to the housing, the biopsy cannula having a side wall, a proximal end, a distal end, and a longitudinal axis extending between the proximal end and the distal end, the side wall having an exterior surface and an interior surface, the interior surface of the side wall defining a lumen, and the side wall having a side port proximal to the distal end that extends through the side wall to the lumen;
a cannula rotation mechanism mounted to the housing, the cannula rotation mechanism having a thumbwheel, a first gear, and a second gear,
the thumbwheel configured to rotate about a rotational axis, the rotational axis being perpendicular to the longitudinal axis of the biopsy cannula,
the first gear mounted in fixed attachment to the thumbwheel,
the second gear mounted in fixed attachment to the exterior surface of the side wall of the biopsy cannula, and
the first gear being in mesh with the second gear such that the first gear is directly drivably engaged with the second gear to rotate the biopsy cannula about the longitudinal axis when the thumbwheel is rotated;
a detent wheel mounted in fixed attachment to the biopsy cannula, the detent wheel having a plurality of detent recesses positioned about the longitudinal axis at predetermined angular positions; and
a lock mechanism mounted to the housing, the lock mechanism including a locking pin biased along a locking axis in constant engagement with the detent wheel, the locking pin including an engagement end having a tapered portion and a non-tapered portion angularly offset from the tapered portion about the locking axis, the locking pin having a first position and a second position, wherein:
in the first position the tapered portion sequentially passes into and out of a respective detent recess of the plurality of detent recesses of the detent wheel as the biopsy cannula is rotated thereby providing at least one of aural, visual and tactile feedback of a progressive rotation of the biopsy cannula, and
in the second position the engagement end rides against the detent wheel and the non-tapered portion lockably engages a next detent recess of the plurality of detent recesses of the detent wheel as the biopsy cannula is rotated to lock the biopsy cannula from further rotation.

7. A biopsy apparatus, comprising:
a housing;
a biopsy cannula mounted to the housing, the biopsy cannula having a side wall, a proximal end, a distal end, and a longitudinal axis extending between the proximal end and the distal end, the side wall having an exterior surface and an interior surface, the interior surface of the side wall defining a lumen, and the side wall having a side port proximal to the distal end that extends through the side wall to the lumen;
a cannula rotation mechanism mounted to the housing, the cannula rotation mechanism having a thumbwheel, a first gear, and a second gear,
the thumbwheel configured to rotate about a rotational axis, the rotational axis being perpendicular to the longitudinal axis of the biopsy cannula,
the first gear mounted in fixed attachment to the thumbwheel,
the second gear mounted in fixed attachment to the exterior surface of the side wall of the biopsy cannula, and
the first gear being in mesh with the second gear such that the first gear is directly drivably engaged with the second gear to rotate the biopsy cannula about the longitudinal axis when the thumbwheel is rotated;
a detent wheel mounted in fixed attachment to the biopsy cannula for coaxial rotation with the biopsy cannula about the longitudinal axis, the detent wheel having a circumferential surface and a plurality of detent recesses formed through the circumferential surface and extending radially toward the longitudinal axis, the plurality of detent recesses being positioned about the longitudinal axis at predetermined angular positions; and
a lock mechanism having a locking pin biased along a locking axis in constant engagement with the detent wheel, the locking pin including an engagement end having a tapered portion and a non-tapered portion angularly offset from the tapered portion about the locking axis,
the locking pin having a first rotational position relative to the locking axis wherein the engagement end rides along the circumferential surface of the detent wheel and the tapered portion sequentially passes into and out of a respective detent recess of the plurality of detent recesses of the detent wheel as the biopsy cannula is rotated thereby providing at least one of aural, visual and tactile feedback of a progressive rotation of the biopsy cannula, and
the locking pin having a second rotational position relative to the locking axis wherein the engagement end rides along the circumferential surface of the detent wheel and the non-tapered portion lockably engages a next detent recess of the plurality of detent recesses of the detent wheel as the biopsy cannula is rotated to lock the biopsy cannula from further rotation.

8. A biopsy apparatus, comprising:
a driver assembly having a housing configured to be grasped by a user;
a biopsy probe drivably coupled to the driver assembly, the biopsy probe including a biopsy cannula having a cylindrical side wall, a proximal end, a distal end and a longitudinal axis extending between the proximal end and the distal end, the cylindrical side wall defining a lumen and having a side port located near the distal end that extends through the side wall to the lumen;
a cannula rotation mechanism mounted to the housing, the cannula rotation mechanism having a thumbwheel, a first gear, and a second gear,
the thumbwheel configured to rotate about a rotational axis, the rotational axis being perpendicular to the longitudinal axis of the biopsy cannula,
the first gear mounted in fixed attachment to the thumbwheel, the second gear mounted in fixed attachment to the biopsy cannula, and the first gear being in mesh with the second gear such that the first gear is directly drivably engaged with the second gear to rotate the biopsy cannula about the longitudinal axis when the thumbwheel is rotated;

a detent wheel mounted in fixed attachment to the biopsy cannula, the detent wheel having a plurality of detent recesses positioned about the longitudinal axis at predetermined angular positions; and an engagement element biased by a spring to be in constant engagement with the detent wheel to sequentially engage each of the plurality of detent recesses to produce at least one of tactile and aural feedback each time the engagement element engages one of the plurality of detent recesses.

9. The biopsy apparatus of claim 8, wherein the biopsy probe is configured for releasable attachment to the housing.

10. The biopsy apparatus of claim 8, configured such that a user rotates the thumbwheel while grasping the housing to effect a manual rotation of the biopsy cannula to position the side port of the biopsy cannula at a desired rotational position about the longitudinal axis.

11. A biopsy apparatus, comprising:

a driver assembly having a housing configured to be grasped by a user;

a biopsy probe drivably coupled to the driver assembly, the biopsy probe including a biopsy cannula having a cylindrical side wall, a proximal end, a distal end and a longitudinal axis extending between the proximal end and the distal end, the cylindrical side wall defining a lumen and having a side port located near the distal end that extends through the side wall to the lumen;

a cannula rotation mechanism mounted to the housing, the cannula rotation mechanism having a thumbwheel, a first gear, and a second gear, the thumbwheel configured to rotate about a rotational axis, the rotational axis being perpendicular to the longitudinal axis of the biopsy cannula, the first gear mounted in fixed attachment to the thumbwheel, the second gear mounted in fixed attachment to the biopsy cannula, and the first gear being in mesh with the second gear such that the first gear is directly drivably engaged with the second gear to rotate the biopsy cannula about the longitudinal axis when the thumbwheel is rotated;

a detent wheel mounted in fixed attachment to the biopsy cannula, the detent wheel having a plurality of detent recesses positioned about the longitudinal axis at predetermined angular positions;

an engagement element biased in constant engagement with the detent wheel to sequentially engage each of the plurality of detent recesses to produce at least one of tactile and aural feedback each time the engagement element engages one of the plurality of detent recesses; and a lock mechanism mounted to the housing, the lock mechanism including a locking pin biased along a locking axis in constant engagement with the detent wheel, the locking pin including an engagement end having a tapered portion and a non-tapered portion angularly offset from the tapered portion about the locking axis, the locking pin having a first position and a second position, wherein:

in the first position the tapered portion sequentially passes into and out of a respective detent recess of the plurality of detent recesses of the detent wheel as the biopsy cannula is rotated thereby providing at least one of aural, visual and tactile feedback of a progressive rotation of the biopsy cannula, and in the second position the engagement end rides along the detent wheel and the non-tapered portion lockably engages a next detent recess of the plurality of detent recesses of the detent wheel as the biopsy cannula is rotated to lock the biopsy cannula from further rotation.

12. A biopsy apparatus, comprising:

a driver assembly having a housing configured to be grasped by a user;

a biopsy probe drivably coupled to the driver assembly, the biopsy probe including a biopsy cannula having a cylindrical side wall, a proximal end, a distal end and a longitudinal axis extending between the proximal end and the distal end, the cylindrical side wall defining a lumen and having a side port located near the distal end that extends through the side wall to the lumen;

a cannula rotation mechanism mounted to the housing, the cannula rotation mechanism having a thumbwheel, a first gear, and a second gear, the thumbwheel configured to rotate about a rotational axis, the rotational axis being perpendicular to the longitudinal axis of the biopsy cannula, the first gear mounted in fixed attachment to the thumbwheel, the second gear mounted in fixed attachment to the biopsy cannula, and the first gear being in mesh with the second gear such that the first gear is directly drivably engaged with the second gear to rotate the biopsy cannula about the longitudinal axis when the thumbwheel is rotated;

a detent wheel mounted in fixed attachment to the biopsy cannula for coaxial rotation with the biopsy cannula about the longitudinal axis, the detent wheel having a circumferential surface and a plurality of detent recesses formed through the circumferential surface and extending radially toward the longitudinal axis, the plurality of detent recesses being positioned about the longitudinal axis at predetermined angular positions; and a lock mechanism having a locking pin biased along a locking axis in constant engagement with the detent wheel, the locking pin including an engagement end having a tapered portion and a non-tapered portion angularly offset from the tapered portion about the locking axis, the locking pin having a first rotational position relative to the locking axis wherein the engagement end rides along the circumferential surface of the detent wheel and the tapered portion sequentially passes into and out of a respective detent recess of the plurality of detent recesses of the detent wheel as the biopsy cannula is rotated thereby providing at least one of aural, visual and tactile feedback of a progressive rotation of the biopsy cannula, and the locking pin having a second rotational position relative to the locking axis wherein the engagement end rides along the circumferential surface of the detent wheel and the non-tapered portion lockably engages a next detent recess of the plurality of detent recesses of the detent wheel as the biopsy cannula is rotated to lock the biopsy cannula from further rotation.

* * * * *